(12) United States Patent
Chen et al.

(10) Patent No.: US 7,048,712 B2
(45) Date of Patent: *May 23, 2006

(54) POLYMER BLENDS FOR USE IN MAKING MEDICAL DEVICES INCLUDING CATHETERS AND BALLOONS FOR DILATATION CATHETERS

(75) Inventors: Ziyun Chen, Santa Clara, CA (US); Tai Cheng, Mountain View, CA (US); Ketan Muni, San Jose, CA (US); Udayan Patel, San Jose, CA (US); Robert Saltman, Redwood City, CA (US)

(73) Assignee: Advanced Cardiovascular Systems, Inc., Santa Clara, CA (US)

( * ) Notice: Subject to any disclaimer, the term of this patent is extended or adjusted under 35 U.S.C. 154(b) by 193 days.

This patent is subject to a terminal disclaimer.

(21) Appl. No.: 10/389,150

(22) Filed: Mar. 14, 2003

(65) Prior Publication Data

US 2003/0232931 A1    Dec. 18, 2003

Related U.S. Application Data

(60) Division of application No. 09/453,984, filed on Dec. 2, 1999, now Pat. No. 6,796,958, which is a continuation-in-part of application No. 08/856,733, filed on May 15, 1997, now Pat. No. 6,013,728, which is a continuation of application No. 08/481,875, filed on Jun. 7, 1995, now abandoned, which is a division of application No. 08/280,764, filed on Jul. 25, 1994, now Pat. No. 5,554,120.

(51) Int. Cl.
*A61M 25/10* (2006.01)

(52) U.S. Cl. .............................. 604/96.01; 604/99.04; 604/264; 525/183; 525/184; 525/425; 525/432

(58) Field of Classification Search ............ 604/96.01, 604/99.04, 264; 525/183, 184, 425, 432
See application file for complete search history.

(56) References Cited

U.S. PATENT DOCUMENTS

| | | | | |
|---|---|---|---|---|
| 5,433,713 A | * | 7/1995 | Trotta | .......................... 604/264 |
| 5,554,120 A | * | 9/1996 | Chen et al. | ............... 604/96.01 |
| 5,556,383 A | * | 9/1996 | Wang et al. | ............ 604/103.11 |
| 5,747,591 A | * | 5/1998 | Chen et al. | .................. 525/183 |
| 5,849,846 A | * | 12/1998 | Chen et al. | .................. 525/166 |
| 6,796,958 B1 | * | 9/2004 | Chen et al. | .................. 525/183 |

* cited by examiner

*Primary Examiner*—Jeffrey B. Robertson
(74) *Attorney, Agent, or Firm*—Fulwider Patton LLP

(57) ABSTRACT

A combination of polymeric components provides desired characteristics in forming medical instruments such as catheters and balloons for dilatation catheters. For example, a balloon material is formed from a blend of polymeric components, including a first crystalline polymeric component and a second softening polymeric component. Where the first two components are generally incompatible, the balloon material can also include a third compatibilizing agent to facilitate blending the first two polymeric components together.

4 Claims, No Drawings

POLYMER BLENDS FOR USE IN MAKING MEDICAL DEVICES INCLUDING CATHETERS AND BALLOONS FOR DILATATION CATHETERS

This is a divisional of application Ser. No. 09/453,984 filed Dec. 2, 1999, now U.S. Pat. No. 6,796,958, which is a continuation of application Ser. No. 08/856,733 filed May 15, 1997, now U.S. Pat. No. 6,013,728, which is a continuation of Ser. No. 08/481,875, filed Jun. 7, 1995, now abandoned, which is a divisional of Ser. No. 08/280,764, filed Jul. 25, 1994, now U.S. Pat. No. 5,554,120, all of which are incorporated by reference.

BACKGROUND OF THE INVENTION

1. Field of the Invention

This invention relates generally to a novel polymer blend that can be extruded, molded, or otherwise formed into articles of manufacture having certain desired characteristics. As examples, the polymer blend of the invention can be processed to form medical catheters and more particularly concerns a balloon material for medical balloon dilatation catheters made from blends of a first crystalline polymer component, and a second softening polymer component. The balloon material can also include a third compatibilizing polymer component. While the invention herein relates generally to polymer blends, it will be discussed in terms of preferred end uses in medical devices such as catheters and dilatation balloons. The subsequent discussion is not meant to be limiting and is by way of examples and preferred uses.

2. Description of Related Art

Catheters are well known for their usefulness in medical applications and in particular angioplasty procedures, for opening blood vessels or other passageways in the body that may be blocked by obstructions or stenosis. Dilatation catheters are generally formed from thin, flexible tubing having an inflatable balloon at or near a distal tip of the tubing that can be inflated with fluid pressure communicated to the balloon through a lumen of the tubing. In a typical angioplasty procedure, the balloon dilatation catheter is passed through the vasculature to the location of a stenosis in an artery, and the balloon is inflated to a predetermined size and shape to open the blocked artery.

It is desirable for balloons of balloon dilatation catheters to be capable of inflating to a diameter of typically five to six times their uninflated diameter in order to be able to open an obstructed vessel. Other desirable properties of balloons for such balloon dilatation catheters include strength, softness, flexibility and a thin, low profile which are important for achieving the performance characteristics of folding in an uninflated state, tracking, crossing and recrossing the area of the obstruction or stenosis in a vessel in an uninflated state. In addition, properties of burst strength, compliance, fatigue have been increasingly important in the continuing effort to create thinner, lower profile balloons for balloon dilatation catheters with an ability to track, cross and recross increasingly narrow passages in obstructed vessels. For purposes of this description, the ability to cross is defined as the ability of a balloon of a balloon dilatation catheter to pass through a stenosis; the ability to recross is defined as the ability of the balloon of a balloon dilatation catheter to pass through a stenosis more than once, or to pass through more than one stenosis; and the ability to track is defined as the ability of balloon of a balloon dilatation catheter to pass over a guidewire through the tortuous curves of the vasculature, in being guided to and from the location of a stenosis.

Polymeric materials that have been used for making medical devices, catheters, dilatation catheters, and balloons for balloon dilatation catheters include polyethylene, polyolefins, polyvinyl chloride, polyester, polyimide, polyethylene terephthalate (PET), polyamides, nylon, polyurethane, and the like. Balloons made of soft polyolefin or ethylene copolymers materials are typically foldable, and track and cross well, so that they can often be used more than once, and can be used to cross multiple lesions. However, such balloons also commonly have high balloon compliance and low burst strengths, with ratings of rated burst pressure of about 8–9 atm, and a mean burst pressure of about 10–15 atm. Balloons made from polyethylene terephthalate (PET) are commonly stronger, with a higher rated burst pressure of about 14–18 atm, and a mean burst pressure of about 18–25 atm. However, dilatation catheter balloons made of PET are generally stiff, not readily foldable and refoldable, and are susceptible to acquiring defects from mechanical handling. Dilatation catheter balloons made of PET are also susceptible to pin-hole failures that can cause jet-streaming of pressurized fluid within an artery, and can lead to a dissection of the artery. As a result, to reduce the likelihood of pin-hole failures, clinical applications of balloons made of this type of material have generally been limited to thicker balloons that are commonly limited to a single use, and for crossing a single lesion.

Examples of prior art compositions that may be suitable in forming medical devices such as catheters, dilatation catheters, and balloon materials for use in angioplasty procedures include U.S. Pat. No. 4,753,980 (Deyrup); U.S. Pat. No. 4,172,859 (Epstein); U.S. Pat. No. 5,091,478 (Saltman); U.S. Pat. No. 5,306,246 (Sahatjian et al.); U.S. Pat. No. 4,254,774 (Boretos); U.S. Pat. No. 4,964,409 (Tremulis); and U.S. Pat. No. 5,017,325 (Jackowski et al.), all of which are incorporated herein by reference. These references are presented by way of example only and are not intended to be exhaustive of the prior art.

It would be desirable to provide a polymeric blend for balloons for balloon dilatation catheters with a combination of the best features of the softer balloon materials and the stronger balloon materials, including good flexibility, folding, track, cross and recross, with a thin, low profile, high resistance to fatigue, low compliance, and high burst strength, with a lower susceptibility to defects through mechanical handling, and a lower susceptibility to pin-hole defects, compared with balloons made from PET. The present invention meets these needs.

SUMMARY OF THE INVENTION

Briefly, and in general terms, the present invention provides for a catheter and/or balloon material formed from a blend of polymeric components that has surprisingly high rated and mean burst pressure characteristics, low compliance and excellent fatigue resistance, along with excellent folding and performance characteristics, such as track, cross and recross, allowing for construction of dilatation catheter balloons with the ability to cross multiple lesions.

The invention accordingly provides for a catheter and/or balloon material formed from a blend composition of a first crystalline polymeric component and a second softening polymeric component. When the first and second polymeric components are essentially incompatible in that they are immiscible, and do not normally bond together well, a third compatibilizing agent that helps to strengthen the interface between the two incompatible materials and to facilitate blending of the first two polymeric components can be added to the balloon material.

The first polymeric component generally consists of about 10–95% by weight of the total blend composition, and in one preferred embodiment can be a polyester prepared from the group of dicarboxylic acids selected from aromatic dicarboxylic acids having from 8 to 14 carbon atoms and aliphatic dicarboxylic acids having from 2 to 12 carbon atoms, and at least one glycol selected from the group consisting of glycols having the formula $HO(CH_2)_nOH$, where n is an integer from 2 to 10, neopentyl glycol and cyclohexane dimethanol. In an alternative embodiment, the first polymeric component can be a branched or straight chain polyamide having a molecular weight of at least about 5000. The second polymeric component generally consists of about 5–90% by weight of the total blend composition, is selected to have a Shore hardness less than 75 D, and preferably less than 55D, and is selected from the group consisting of ethylene copolymers, polyolefins having a density less than 0.93, polyester block copolymers and polyamide block copolymers. The third polymeric component generally consists of an amount of a compatibilizing ethylene copolymer that is less than about 2.5% by weight of the total balloon material blend, and preferably about 0.25% to about 2.5% by weight of the total balloon material blend, and has the formula E/X/Y where E is ethylene; X is an $\alpha,\beta$-ethylenically unsaturated monomer derived from at least one of vinyl acetate, alkylacrylate, alkylmethacrylate, alkyl vinyl ether, carbon dioxide, sulfur dioxide, or mixtures thereof, where the alkyl groups contain 1–12 carbon atoms; and Y is an $\alpha,\beta$-ethylenically unsaturated monomer containing a reactive group that will form a covalent bond with the first polymeric component. Alternatively, suitable catheter and/or balloon materials can be prepared that contain up to about 20% by weight of the third polymeric component.

The first polymeric component preferably comprises about 60–77% of the total blend composition, and in a preferred embodiment is selected from the group consisting of polyethylene-terephthalate, polybutylene-terephthalate, glycol modified polyethylene-terephthalate, 1,4-cyclohexylene dimethylene terephthalate/isophthalate copolymer, linear homopolymer esters derived from aromatic dicarboxylic acids and glycols of the general formula $HO(CH_2)_nOH$ where n is an integer from 2 to 10. In a preferred aspect of the invention, the second polymeric component is a softening ethylene copolymer comprising about 23–40% by weight of the total blend composition, and contains ethylene and at least one other monomer selected from the group consisting of $\alpha, \beta$-ethylenically unsaturated monomers, carbon monoxide, and sulfur dioxide. In one particularly preferred embodiment, the softening ethylene copolymer has the formula E'X' or E'X'Y', where E' is ethylene, and is about 60–85% by weight of the ethylene copolymer, and where X' is about 15–40% by weight of the ethylene copolymer, and X' is selected from the group consisting of methylacrylate, ethylacrylate, propylacrylate, butylacrylate, and mixtures thereof, and Y', if present, is an $\alpha,\beta$-ethylenically unsaturated monocarboxylic acid, di-acid or anhydride comprising about 0.5–15% by weight of the ethylene copolymer. Examples of Y' include but are not limited to acrylic acid, methacrylic acid, fumaric acid and maleic anhydride. Where one of the X' or Y' monomers is an acid containing moiety, the polymer can also be at least partially neutralized with an ion selected from the group of sodium, potassium, zinc, lithium, calcium, and ammonium. In a preferred embodiment, in the third polymeric component, X is selected from the group consisting of vinyl acetate, methylacrylate, butylacrylate, and methyl vinyl ether, Y is an $\alpha,\beta$-ethylenically unsaturated monomer containing a reactive group selected from the group consisting of epoxide, maleic anhydride, isocyanate, or oxazoline. In one preferred embodiment, Y is selected from the group consisting of glycidyl acrylate, glycidyl methacrylate, and epoxide containing copolymerizable monomers. In one currently particularly preferred embodiment, in the third polymeric component, E is ethylene, and is 67% by weight of the compatibilizing ethylene copolymer; X is selected from the group of methylacrylate, ethylacrylate, and butylacrylate, and is about 15–30% by weight of the compatibilizing agent; and Y is selected from the group consisting of glycidyl acrylate and glycidyl methacrylate, and is about 8% by weight of the compatibilizing agent.

These and other aspects and advantages of the invention will become apparent from the following detailed description of the preferred embodiments.

DETAILED DESCRIPTION OF THE PREFERRED EMBODIMENTS

The present invention relates to a polymer blend having certain characteristics generally desirable in medical devices. The polymer blend described herein is particularly suitable for use in forming medical products such as catheters, dilatation catheters, and preferably balloon material for use with catheters.

While dilatation catheter balloons made of soft polyolefin or ethylene copolymer materials have generally good performance characteristics, such balloons also commonly have high balloon compliance and low burst strengths. Dilatation catheter balloons made from strong polymeric materials such as polyethylene terephthalate (PET) have higher rated and mean burst pressures, but are generally stiff, not readily foldable and refoldable, and are susceptible to acquiring defects from mechanical handling, and are susceptible to pin-hole failures that can seriously injure the vasculature of a patient. While the embodiments discussed herein refer generally to balloon materials, it is to be understood that the invention relates to catheters as well having the polymer blends as described.

The invention accordingly is embodied in a balloon material for balloon dilatation catheters with a combination of the best features of the softer balloon materials and the stronger balloon materials, including high burst strength, low compliance, good flexibility, high resistance to fatigue, the ability to fold, track, cross and recross well, and with a lower susceptibility to defects through mechanical handling, and a lower susceptibility to pin-hole defects, compared with balloons made from PET. The balloon material is formed from a blend of three polymeric components, comprising a strong polymeric component, a softening polymeric component that are generally incompatible, and a compatibilizing polymeric component that forms a covalent bond with one of the first two polymeric components, and prevents the first two polymeric components from separating when formed as a balloon for a balloon dilatation catheter.

The first polymeric component, component A, is preferably a relatively strong crystalline polymer, preferably comprising about 60–77% of the total blend composition, although blend compositions of the invention comprising as little as 10% or as much as 95% of the total blend composition may also be suitable. In one currently preferred embodiment, component A comprises PET, but can also comprise other polyesters, or polyamides. Other polyesters which can be used as component A include polyesters prepared from an aromatic dicarboxylic acid having from 8 to 14 carbon atoms and at least one glycol, including those having the formula $HO(CH_2)_nOH$ where n is an integer of 2 to 10, neopentyl glycol and cyclohexane dimethanol. The dicarboxylic acid may also be an aliphatic dicarboxylic acid having from 2 to 12 carbon atoms. Examples of other suitable polyesters include, but are not limited to, polybutylene-terephthalate (PBT), glycol modified PET (PETG), 1,4-cyclohexylene dimethylene terephthalate/isophthalate copolymer and other linear homopolymer esters derived from aromatic dicarboxylic acids and glycols of the general formula $HO(CH_2)_nOH$ where n is an integer from 2 to 10. Such aromatic dicarboxylic acids include isophthalic, bibenzoic, naphthalene-dicarboxylic including the 1,5-; 2,6-; and 2,7-naphthalenedicarboxylic acids; 4,4'-diphenylenedicarboxylic acid; bis(p-carboxyphenyl) methane; ethylene-bis-p-benzoic acid; 1,4-tetramethylene bis(p-oxybenzoic) acid; ethylene bis(p-oxybenzoic) acid; 1,3-trimethylene bis(p-oxybenzoic) acid; and 1,4-tetramethylene bis(p-oxybenzoic) acid. Preferred glycols include ethylene glycol; 1,3-trimethylene glycol; 1,4-tetramethylene glycol; 1,6-hexamethylene glycol; 1,8-octamethylene glycol; 1,10-decamethylene glycol; 2,2-dimethyl-1,3-propane diol; 1,3-propylene glycol; 1,4-butylene glycol; neopentyl glycol and cyclohexane dimethanol.

Polyamides which are suitable for use as component A include branched or straight chain polyamides having a molecular weight of at least 5000, and commonly referred to as nylons; produced by condensation of equimolar amounts of a saturated dicarboxylic acid containing from 4 to 12 carbon atoms with a diamine, in which the diamine contains from 4 to 12 carbon atoms. Examples of suitable polyamides include, but are not limited to, nylons such as polyhexamethylene adipamide (nylon 6,6), polyhexamethylene azelaamide (nylon 6,9), polyhexamethylene sebacamide (nylon 6,10), polyhexamethylene dodecanoamide (nylon 6,12), nylon 6, nylon 11, and nylon 12. Other polyamides that can be suitable include polyamide block copolymers such as those sold under the trade name "PEBAX" by Atochem; polyamides including polyamides produced by the ring opening of lactams such as polycaprolactam, polylauric lactam, poly-11-amino-undecanoic acid, and bis(paraminocyclohexyl) methane dodecanoamide; and polyamides prepared by the copolymerization or terpolymerization of such polymers. The polyamides preferably have a melting point in excess of 200° C.

The second polymeric component, component B, is selected to be a softening polymer, preferably comprising about 23–40% by weight of the total balloon material composition, although blends of the balloon material comprising as little as 5% of component B and as much as 90% of the total blend composition may also be suitable. In a currently preferred embodiment, component B comprises a softening polymer component having a Shore hardness less than 75 D, and preferably less than 55D, and is preferably an elastomeric ethylene copolymer selected from the group of ethylene copolymers comprising ethylene and at least one other monomer selected from the group of $\alpha,\beta$-ethylenically unsaturated monomers, carbon monoxide (CO), sulfur dioxide ($SO_2$). Component B is most preferably an elastomeric ethylene copolymer having the formula E'X' or E'X'Y', where E' is ethylene and comprises about 60–85% by weight of the ethylene copolymer, X' is acrylate or methacrylate monomer, comprising about 15–4.0% of the ethylene copolymer, and Y', if present, is an $\alpha,\beta$-ethylenically unsaturated monocarboxylic acid, di-acid or anhydride comprising about 0.5–15% by weight of the ethylene copolymer.

Examples of Y' include but are not limited to acrylic acid, methacrylic acid, fumaric acid and maleic anhydride. Other polymeric materials that may be suitable for use as component B include, but are not limited to, polyester block copolymers (containing one or more of the following glycols) comprising hard segments of polyethylene-terephthalate or polybutylene-terephthalate, and soft segments of polyether such as polyethylene glycol, polypropylene glycol or polytetramethylene glycol ethers, such as those available under the tradename "HYTREL" from DuPont. Long chain glycols which can be used to prepare such copolyester polymers include poly(alkylene oxide) glycols in which the alkylene group has 2–10 carbon atoms, such as poly(ethylene oxide) glycol, poly(1,2- and 1,3-propylene oxide) glycol, poly(tetramethylene oxide) glycol, poly(pentamethylene oxide) glycol, poly(hexamethylene oxide) glycol, poly(heptamethylene oxide) glycol, poly(octamethylene oxide) glycol, poly(nonamethylene oxide) glycol, and poly(1,2-butylene oxide) glycol, random or block copolymers of ethylene oxide and 1,2-propylene oxide, and poly-formals prepared by reacting formaldehyde with glycols, such as propylene glycol, or mixtures of glycols, such as a mixture of tetramethylene and pentamethylene glycols, and glycols formed from dicarboxymethyl acids of poly(alkylene oxides); polyetherimide esters such as those produced under the tradename "LOMOD" by General Electric; polyesters available from Dutch State Mines under the trade name "ARNITEL"; polyamide block copolymers, such as those available from Atochem under the tradename "PEBAX"; and polyolefins having a density less than 0.93, including elastomeric ethylene-propylene copolymers, linear low density polyethylene (LLDPE), and linear low density polyethylene (LLDPE) including maleic anhydride.

The most preferred ethylene copolymers which can be used as component B include, but are not limited to, ethylene/methylacrylate/sulfur dioxide (E/MA/SO$_2$), ethylene/butylacrylate/carbon monoxide (E/BA/CO) ethylene/methylacrylate (E/MA), ethylene ethylacrylate (E/EA), ethylene/butylacrylate (E/BA), ethylene/vinylacetate (E/VA), ethylene/methacrylic acid (E/MAA or E/AA), ethylene/butylacrylate/methacrylic acid (E/BA/MAA or E/BA/AA), ethylene/methylacrylate/methacrylic acid (E/MA/MAA or E/MA/AA), ethylene/butylacrylate/maleic anhydride (E/BA/Manh) or ethylene/methylacrylate/maleic anhydride (E/MA/Manh). Where one of the $\alpha,\beta$-ethylenically unsaturated monomers is an acid containing moiety, the polymer can be partially neutralized with an ion such as Na+, K+, Zn++, Li+, Ca++, NH4+, or the like. The acid groups in the unsaturated mono-carboxylic acid are neutralized from 0–80% by at least one metal ion selected from the group consisting of sodium, zinc, magnesium, calcium, potassium, and lithium. The third polymeric component, component C, is preferably an ethylene copolymer that functions as a compatibilizing agent or surfactant, in that it forms a covalent bond with the first polymeric component, and blends compatibly with the second polymeric component. Component C preferably comprises from zero to about 2.5% of the total blend composition, having the formula E/X/Y, where E is about 67%, X is about 25%, and Y is about 8% by weight of the compatibilizing ethylene copolymer, and E is ethylene, X is an $\alpha,\beta$-ethylenically unsaturated monomer derived from at least one of alkylacrylate, alkylmethacrylate, alkyl vinyl ether, carbon dioxide, sulfur dioxide, or mixtures thereof, where the alkyl groups contain 1–12 carbon atoms, such as vinyl acetate, methylacrylate, butylacrylate, and methyl vinyl ether. X can, for example be a moiety derived from at least one of alkyl acrylate, alkyl methacrylate, alkyl vinyl ether, carbon monoxide, sulfur dioxide, or mixtures thereof. More specifically, X can, for example, consist of 0–35 weight percent of a moiety derived from at least one alkyl acrylate, alkyl methacrylate, or mixtures thereof where the alkyl groups contain 1–8 carbon atoms.

Y is an $\alpha,\beta$-ethylenically unsaturated monomer containing a reactive group, such as epoxide, maleic anhydride, isocyanate, or oxazoline, for example, that forms a covalent bond with said first polymeric component. In one preferred embodiment, Y is selected from the group consisting of glycidyl methacrylate and glycidyl acrylate, maleic anhydride, and isocyanato-ethylmethacrylate.

In one currently preferred embodiment the first polymeric component of the balloon material blend comprises about 70–77% by weight PET; about 23–30% by weight of component B, which comprises an ethylene copolymer having the formula E'X', where E' is ethylene, and is about 75% by weight of the ethylene copolymer, and X' is selected from the group of ethylene methylacrylate, ethylene ethylacrylate, ethylene propylacrylate, and ethylene butylacrylate, and is about 25% by weight of the ethylene copolymer; and from about 0.25% to about 2.5% by weight of component C, which is an ethylene copolymer having the formula EXY, where E is ethylene, and is 67% by weight of component C; X is selected from the group of ethylene acrylate and ethylene methylacrylate, and is about 25% by weight of component C; and Y is selected from the group consisting of glycidyl methacrylate, glycidyl ethylacrylate, and glycidyl butylacrylate, and is about 8% by weight of component C. The second polymeric component, component B, is most preferably an elastomeric ethylene copolymer selected from the group consisting of ethylene/methylacrylate, ethylene/ethylacrylate, ethylene/butylacrylate, ethylene/methylacrylate/maleic anhydride, ethylene/ethylacrylate/maleic anhydride, and ethylene/butylacrylate/maleic anhydride; and the third polymeric component, component C, is most preferably an ethylene acrylate ester where X is selected from methyl acrylate, ethyl acrylate and butyl acrylate, and Y is selected from the group consisting of glycidyl acrylate and glycidyl methacrylate.

In addition, in a preferred aspect of the invention, the balloon material of the invention can advantageously be irradiated using ionizing radiation from an electron beam, gamma rays, ultraviolet light, or a molecular beam, to significantly alter the properties of the balloon material to provide improved balloon performance such as higher burst pressures. For example, where the balloon material was subjected to an electron beam of about 10–100 MRads and energies of 100–200,000 keV, higher burst strengths and higher fatigue strengths were obtained from the balloon material.

The balloon materials of the invention provide dilatation catheter balloons with the ability to cross multiple lesions, good track, cross, and folding, low compliance with rated burst pressures of about 10–15 atm, and mean burst pressures of about 14–20 atm. Balloons made from the balloon material of the invention also typically have a lower susceptibility to defects through mechanical handling than PET. When exposed to ionizing radiation to toughen the balloon material, the fatigue and burst strengths are substantially increased, to give rated burst pressures of 12–14 atm or greater, mean burst pressures of 19–20 atm, and a compliance of about 0.02–0.03 (mm/atm).

EXAMPLE 1

A polymer blend containing 80 weight % PET Traytuf 9506C manufactured by Shell, and 20 weight % ethylene ethylacrylate (EEA) DPDA 6182 manufactured by Union Carbide, was produced by compounding in a twin screw extruder set for low shear conditions. The PET and EEA were mixed in a weight ratio of 80/20. The PET/EEA mixture was loaded into the hopper of the compounder. The barrel temperatures were set to 410° F. in zone 1, 490° F. in zones 2 and 3, and 480° in zone four and at the head of the barrel, the screw speed was maintained at 150 RPM, and the material was pelletized. Balloon tubing having an inner diameter of 0.018 inches and an outer diameter of 0.036 inches was extruded using the 80/20 PET/EEA blend. The 80/20 PET/EEA blended material was dried. The barrel and die temperatures of the extruder were set, with zone 1 at 390° F., zone 2 at 480° F., zone 3 at 500° F., and the clamp, die 1 and die 2 at 510° F. The melt temperature of the blend was 574° F. Examination with a scanning electron microscope of a portion of the blend before extrusion into balloon tubing showed that the EEA formed spherical particles with a diameter greater than one micron, with poor interfacial adhesion within the PET matrix. A section of the extruded balloon tubing was also examined with a scanning electron microscope, showing that the EEA formed tubules in the extruded balloon tubing that pulled out of the PET matrix.

EXAMPLE 2

The blend of PET and EEA from Example 1 was compounded and blended with 2% of the total blend composition by weight of a third component, E/EA/GMA, as a compatibilizer, available as Lotader AX8660 from AtoChem. Examination with a scanning electron microscope of a portion of the blend before extrusion into balloon tubing showed that the EEA formed a much better dispersion with better interfacial adhesion within the PET matrix, with little or no particle pull-out from the PET matrix. A section of the extruded balloon tubing made from the blend was also examined with a scanning electron microscope, showing that the EEA formed no tubules in the extruded balloon tubing, and that the dispersed particles of EEA were well adhered to the PET matrix. The material had a burst pressure of about 50 psi higher than in Example 1.

EXAMPLES 3–10

Balloon material blends were also formed using PET available as Traytuf 9506C from Shell, with a tensile strength of 7000 psi (non-oriented), and 10000–12000 (oriented), an elongation of 400–500% (after yield), a flexural modulus of 500,000–600,000 psi, and a melting point of 257° C. EEA available as DPDA 6182 from Union Carbide was used in Examples 3–5 and 8–10, with a tensile strength of 2300 psi, elongation of 670%, a flexural modulus of 6400 psi, a melt index of 1.5, a durometer of 91A, a melting point of 85 C, a density of 0.93 and a Vicat Softening index of 64. EMAC available as TC130 from Exxon was used in Examples 6 and 7, with a tensile strength of 1200 psi, an elongation of 1600%, a flexural modulus of 3300 psi, a melt index of 20, a Durometer of 85A, a melting point of 79 C, a density of 0.94 and a Vicat Softening index of 50. Lotryl 24MA005 (EMA) from AtoChem was used as the softening component in Example 10, with a tensile strength of 2910 psi, elongation of 700%, a melt index of 0.5, a Durometer of 84A, a melting point of 70 C, and a Vicat Softening index of 43. Lotader AX8660 (67% E, 25% EA, 8% GMA) from AtoChem was used as the compatibilizing agent in Examples 4–10, with a tensile strength of 509 psi, an elongation of 700%, a melt index of 6.0, a Durometer of 60A, a melting point of 63 C, and a Vicat Softening index of 34.

The blend compositions of Examples 3–10 are listed in Table I below, and were compounded under the compounding conditions noted in Table II and were extruded under the tubing extrusion conditions noted in Table III.

TABLE I

| Example | PET % | EEA % | EMAC % | Lotryl % | Lotader % |
|---------|-------|-------|--------|----------|-----------|
| 3  | 60   | 40   | —    | —  | —   |
| 4  | 78.4 | 19.6 | —    | —  | 2   |
| 5  | 76   | 19   | —    | —  | 5   |
| 6  | 78.4 | —    | 19.6 | —  | 2   |
| 7  | 76   | —    | 19   | —  | 5   |
| 8  | 68.8 | 29.5 | —    | —  | 1.7 |
| 9  | 59.1 | 39.4 | —    | —  | 1.5 |
| 10 | 70   | —    | —    | 28 | 2   |

TABLE II

| | Example | | | | | | |
|---|---|---|---|---|---|---|---|
| | 3 | 4 | 5 | 6 | 7 | 8 | 9 | 10 |
| T1 °F. | 410 | 410 | 410 | 400 | 400 | 400 | 400 | 275 |
| T2 °F. | 490 | 480 | 480 | 480 | 450 | 450 | 450 | 480 |
| T3 °F. | 490 | 480 | 480 | 490 | 490 | 485 | 485 | 535 |
| T4 °F. | 480 | 500 | 500 | 515 | 515 | 500 | 500 | 555 |
| Thead °F. | 480 | 500 | 500 | 515 | 515 | 500 | 500 | 555 |
| RPM | 150 | 150 | 150 | 150 | 150 | 150 | 150 | 150 |
| Dry °F. | 300 | 200 | 200 | 200 | 200 | 200 | 200 | 200 |

TABLE III

| | Example | | | | | |
|---|---|---|---|---|---|---|
| | 3 | 4 | 5 | 6 | 8 | 10 |
| T1 °F. | 390 | 400 | 400 | 370 | 400 | 405 |
| T2 °F. | 480 | 480 | 480 | 430 | 480 | 485 |
| T3 °F. | 500 | 510 | 510 | 480 | 500 | 490 |
| Tclamp °F. | 510 | 510 | 510 | 480 | 500 | 490 |
| Tdie1 °F. | 510 | 510 | 510 | 480 | 500 | 490 |
| Tdie2 °F. | 510 | 510 | 510 | 480 | 500 | 500 |
| I.D. inches | .018 | .020 | .020 | .020 | .020 | .020 |
| O.D. inches | .036 | .040 | .040 | .040 | .040 | .040 |
| Dry °F. | 150 | 150 | 150 | 150 | 150 | 150 |

EXAMPLE 11

In Example 11, a blend composition was compounded according to the method of Example 1. Tubing was extruded with an inner diameter of 0.18 inches, an outer diameter of 0.036 inches, and a double wall thickness (DWT) of 0.00135 inches. The balloon formed from the tubing was subjected to 25 Mrads of radiation, and had a mean burst pressure of 250 psi.

EXAMPLES 12–13

In Examples 12 and 13, a blend composition was compounded according to the method of Example 2. In Example 12, tubing was extruded with an inner diameter of 0.020 inches and an outer diameter of 0.040 inches. Balloons were formed with an outer diameter of 0.119 in., a DWT of 0.0015 in., and were subjected to 40 Mrads of radiation and demonstrated higher burst pressures. For example, the balloon formed from the tubing had a mean burst pressure of 285 psi (19.4 atm). Tubing not subjected to irradiation was formed into a balloon with an outer diameter of 0.1195 in., a DWT of 0.00145 in., and a mean burst pressure of 252 psi (17.1 atm).

EXAMPLES 14–15

In Examples 14 and 15, a polymer blend containing 90 weight % PET Traytuf 9506C manufactured by Shell, and 10 weight percent of an ionomeric resin of ethylene and methacrylic acid, available under the tradename "SURLYN," manufactured by DuPont, were blended. The materials were separately dried. Balloon tubing having an inner diameter of 0.021 inches and an outer diameter of 0.0325 inches was extruded using this 90/10 blend. The barrel and die temperatures of the extruder were set with Zone 1 at 460° F., Zone 2 at 485° F., Zone 3 at 500° F., die 1 at 520° F., die 2 at 520° F.

In Example 14, a balloon was formed and material had a mean burst pressure of 207 psi (14.1 atm).

In Example 15, tubing was formed as in Example 13. The tubing was subjected to 20 Mrads of radiation. The balloons formed had a mean burst pressure of 255 psi (17.3 atm).

It will be apparent from the foregoing that while particular forms of the invention have been illustrated and described, various modifications can be made without departing from the spirit and scope of the invention. Accordingly, it is not intended that the invention be limited, except as by the appended claims.

What is claimed:

1. A catheter having a balloon formed of a polymeric material blend, the blend comprising:
    a) a polyamide first polymeric material, which is about 10% to about 95% by weight of the total blend; and
    b) a second polymeric material, which is about 5% to about 90% by weight of the total blend, which is noncompatible with the polyamide first polymeric material, and which has a Shore durometer hardness of less than about 75D.

2. The catheter of claim 1 wherein the first polymeric material is a polyether block amide copolymer.

3. The catheter of claim 1 wherein the first polymeric material is about 60% to about 77% by weight of the total blend.

4. The catheter of claim 1 wherein the blend includes a compatibilizing agent which facilitates blending the first and second polymeric materials.

* * * * *